US005637079A

United States Patent [19]

Miller

[11] Patent Number: 5,637,079

[45] Date of Patent: Jun. 10, 1997

[54] TRACTION APPARATUS

[76] Inventor: Richard P. Miller, 15 Maxworthy Street, Spearwood, Western Australia, Australia

[21] Appl. No.: 454,251

[22] PCT Filed: Oct. 20, 1993

[86] PCT No.: PCT/AU93/00539

§ 371 Date: Jun. 2, 1995

§ 102(e) Date: Jun. 2, 1995

[87] PCT Pub. No.: WO94/08545

PCT Pub. Date: Apr. 28, 1994

[51] Int. Cl.[6] .......... A61F 5/00

[52] U.S. Cl. .......... 602/36; 602/32; 606/241; 601/23

[58] Field of Search .......... 601/23, 24, 90, 601/98; 602/32, 35, 36; 606/241, 242, 245; 482/95, 96, 131, 142, 907

[56] References Cited

U.S. PATENT DOCUMENTS

| | | | |
|---|---|---|---|
| 3,043,591 | 7/1962 | Sellner | 601/24 |
| 4,282,868 | 8/1981 | Riggs | 606/241 |
| 4,583,533 | 4/1986 | Goodley et al. | 602/36 |
| 4,608,969 | 9/1986 | Hamlin | 606/241 |
| 5,163,890 | 11/1992 | Perry, Jr. | 482/142 |
| 5,217,488 | 6/1993 | Wu | 606/241 |

FOREIGN PATENT DOCUMENTS

| | | | |
|---|---|---|---|
| 374803 | 3/1964 | Switzerland | 602/36 |
| 394484 | 11/1965 | Switzerland | 606/242 |
| 1517958 | 10/1989 | U.S.S.R. | 606/241 |

*Primary Examiner*—Richard J. Apley
*Assistant Examiner*—Jeanne M. Clark
*Attorney, Agent, or Firm*—Knobbe, Martens, Olson & Bear LLP

[57] ABSTRACT

A self contained portable traction or back-stretch apparatus (11) comprising a frame assembly (13) with first tensile force application means in the form of two U-shaped members (15) for supporting a person under their arms, and a second tensile force application means (17 or 57) for supporting a person about their waist and hips. The frame assembly (13) is formed of two frames (19) comprising parallel elongate struts (21) and parallel elongate struts (23) connected about a pivot pin (25) in a scissor type relationship. Separation of the force application means (15 and 17 or 57) is limited by a resiliently stretchable mat (37) which also serves to support the weight of a person therebetween. The weight of the person supported in the traction apparatus results in a downward force on the frame assembly (13) which translates to a tensile force applied between the force application means (15 and 17 or 57) and effects traction, providing a degree of intervertebral separation in the person.

16 Claims, 12 Drawing Sheets

TRACTION APPARATUS

This invention relates to a traction apparatus and in particular a traction device for stretching the human back.

For many people, the time spent daily in a vertical posture, subjecting the spine to the compressive effects of gravity, causes discomfort to the back. Some people seek to relieve this discomfort by stretching their back but find it physically difficult to effect the desired stretch.

To seek relief from such discomfort a person may undertake treatment under medical supervision of a doctor, physiotherapist or chiropractor. Such treatment will invariably involve the use of some form of traction to provide a small distance of inter-vertebral separation, for a short or long period of time, in order to effect relief of pain or other symptoms associated with disorders of the spine. A difficulty of these known types of treatment, whether they be administered on a traction couch or table, in a bed, or on a chair, is that they require medical supervision to ensure that they are set up correctly, and generally cannot be set up readily at home, with perhaps the exception of cervical traction in extremely limited circumstances.

There have been other apparatus proposed to stretch a persons back, such as, for example, a product known as "gravity boots", being footwear having a clip on each for engaging a horizontal bar so as to enable the wearer to be suspended upside down from the horizontal bar. In addition, also known are inversion tables, on which a user leans while standing with his or her feet restrained, and by altering their weight over a pivot point may cause the table to rotate thereabout, causing their feet to be displaced to an uppermost position from which their body hangs relieving compressive forces exerted on the spine while so inverted. These proposals have the disadvantage that while they can be employed at home by the general public, they do require a level of athletic ability which can be beyond that of many people who would benefit from the use of the equipment.

It is an object of this invention to alleviate the aforementioned disadvantages by providing a traction apparatus which obviates or mitigates the aforementioned difficulties, or at least provides an alternative.

It is a preferred object of the invention to provide a traction apparatus which can be employed without supervision.

In accordance with one aspect of the present invention there is provided a traction apparatus for vertebral manipulation having a first tensile force application means for engaging the body of a person in proximity to the upper thorax, and having a second tensile force application means for attaching to the body of said person in proximity to the lower lumbar region; said first and second attachment means being supported on respective first and second frame members mounted pivotally about each other, in relative spaced relationship to each other.

The frame members so arranged are adapted to exert a tensile force between the first tensile force application means and the second tensile force application means. The second tensile force application means may include an attachment point located on the second frame member. The tensile force is derived from force applied on the frame members when the traction apparatus is in use, and is derived from force due to gravity applied by the mass of said person. In the most preferred form of the invention the force is applied oblique to the direction of the tensile force, when the traction apparatus is in use. The frame members conveniently may each be in the form of a U shape.

Preferably said frame members are arranged to prescribe spatial movement of said first and second tensile force application means relative to each other.

Preferably said frame members respectively comprise a pair of first elongate struts and a pair of second elongate struts, each strut of said pair being arranged in side by side relationship, each said first elongate strut being pivotally mounted to a respective second elongate strut about an axis located along each strut away from either end thereof.

In this arrangement the first tensile force application means are located proximal to upper portions of the first elongate struts and the second tensile force application means are located proximal to upper ends of said second elongate struts.

Preferably said traction apparatus includes means for limiting distal extent of movement of said first and second tensile force application means relative to each other.

Preferably said limiting means comprises a resilient strap extending between said upper portions of said first and second elongate struts.

Alternatively said limiting means comprises a mat extending between said upper portions of said elongate struts, said mat being resiliently deformable at least in the direction of the extent between said upper portions of said first and second elongate struts.

Preferably said mat is resiliently deformable in a direction extending between parallel elongate struts.

In this arrangement the mat also provides support for the body of the person using the traction apparatus.

Preferably said first tensile force application means comprises a first support means adapted to engage the body of said person about their shoulders and armpits.

Preferably said second tensile force application means comprises a second support means adapted to engage the body of said person about their hips.

Preferably said second support means comprises a belt or girdle adapted to be fastened so as to prevent movement to a position below the hips of a wearer and adapted to be removably fastened to said second frame.

Alternatively said second support means comprises a clamp, preferably adjustable, adapted to engage a person about their hips.

Preferably said clamp is formed in a shape complementary to a portion of the shape of a person about and above their hips. In this manner, when fixed, the clamp will not be able to slip below the hips of the person, thus providing purchase to apply said tensile force.

Preferably said first support means comprises a pair of substantially U-shaped members, one mounted on each said first elongated member.

Preferably said first support means includes restraining portions adapted to abut the flat of the scapulae of said person.

Preferably said first support means also includes a resiliently stretchable strap extending between said restraining portions.

Preferably said traction apparatus includes a first adjustment means to selectively vary the positioning of said first support means. This may take the form of an adjuster for adjustment of the spacing of the first support means to suit different builds and shoulder widths of persons using the traction apparatus, or adjustment for the displacement of the first support means from the axis, or both.

Preferably said first adjustment means comprises an adjustable strut extending from said first elongate struts.

Preferably said traction apparatus includes a second adjustment means to selectively vary the positioning of said second support means. In this manner the spacing of the second support means or attachment means for said second tensile force application means can be adjusted to suit different builds and hip widths of persons using the traction apparatus, or the distance from said second support means or attachment means for said second tensile force application means to said axis may be adjusted, or both.

Preferably said second adjustment means comprises a further adjustable strut extending from said second elongate struts.

In accordance with another aspect of the present invention there is provided a traction apparatus for vertebral manipulation having a first tensile force application means adapted to engage the body of a person in proximity to the upper thorax and having attachment means for a second tensile force application means for engaging the body of said person in proximity to the lower lumbar region, said first tensile force application means and said attachment means being mounted to a frame assembly adapted to present said first tensile force application means and said second tensile force application means uppermost, wherein said frame assembly is adapted to draw said first tensile force application means and said second tensile force application means apart in response to downward forces incident on said first tensile force application means and said second tensile force application means.

The preferred features relating to the limiting means, the support means, and the adjustment means of the first and second aspects of the invention are equally preferred in this aspect of the invention.

The invention will be better understood by referring to the following description of four specific embodiments thereof in which.

Figure 3:
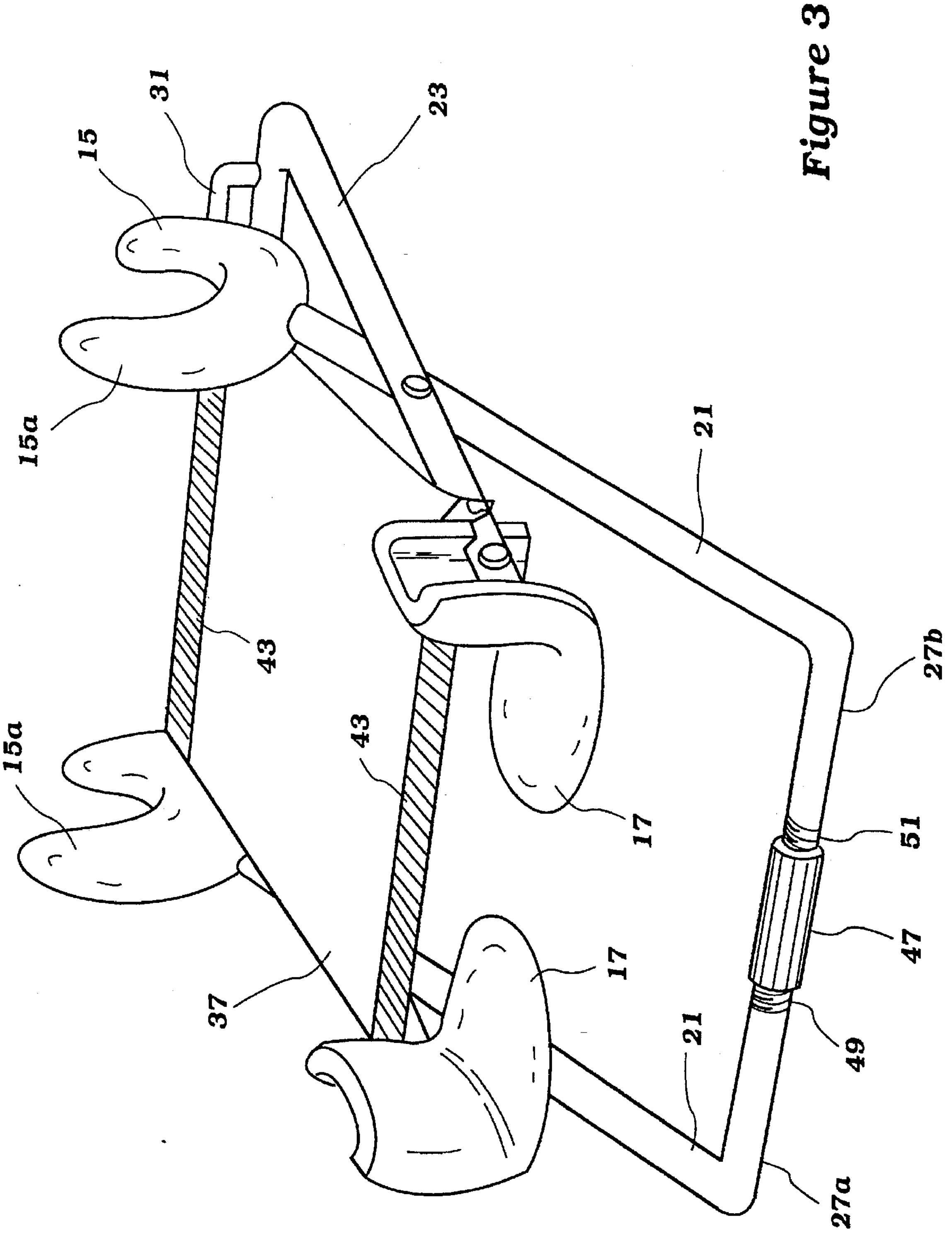
FIG. 3 is a perspective view of a traction apparatus according to the second embodiment.
Figure 4:
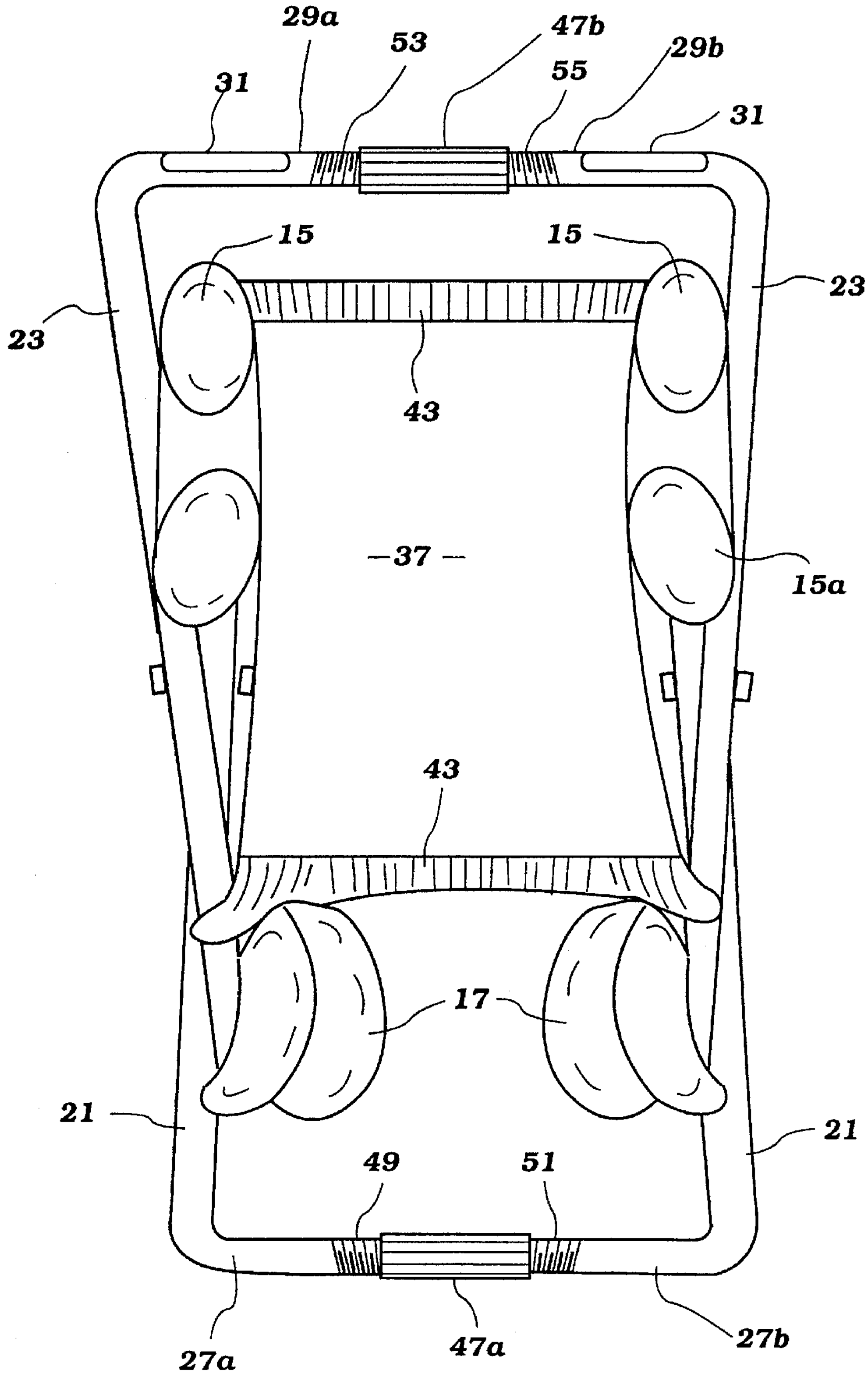
FIG. 4 is a plan view of the traction apparatus shown in FIG. 3.
Figure 4A:
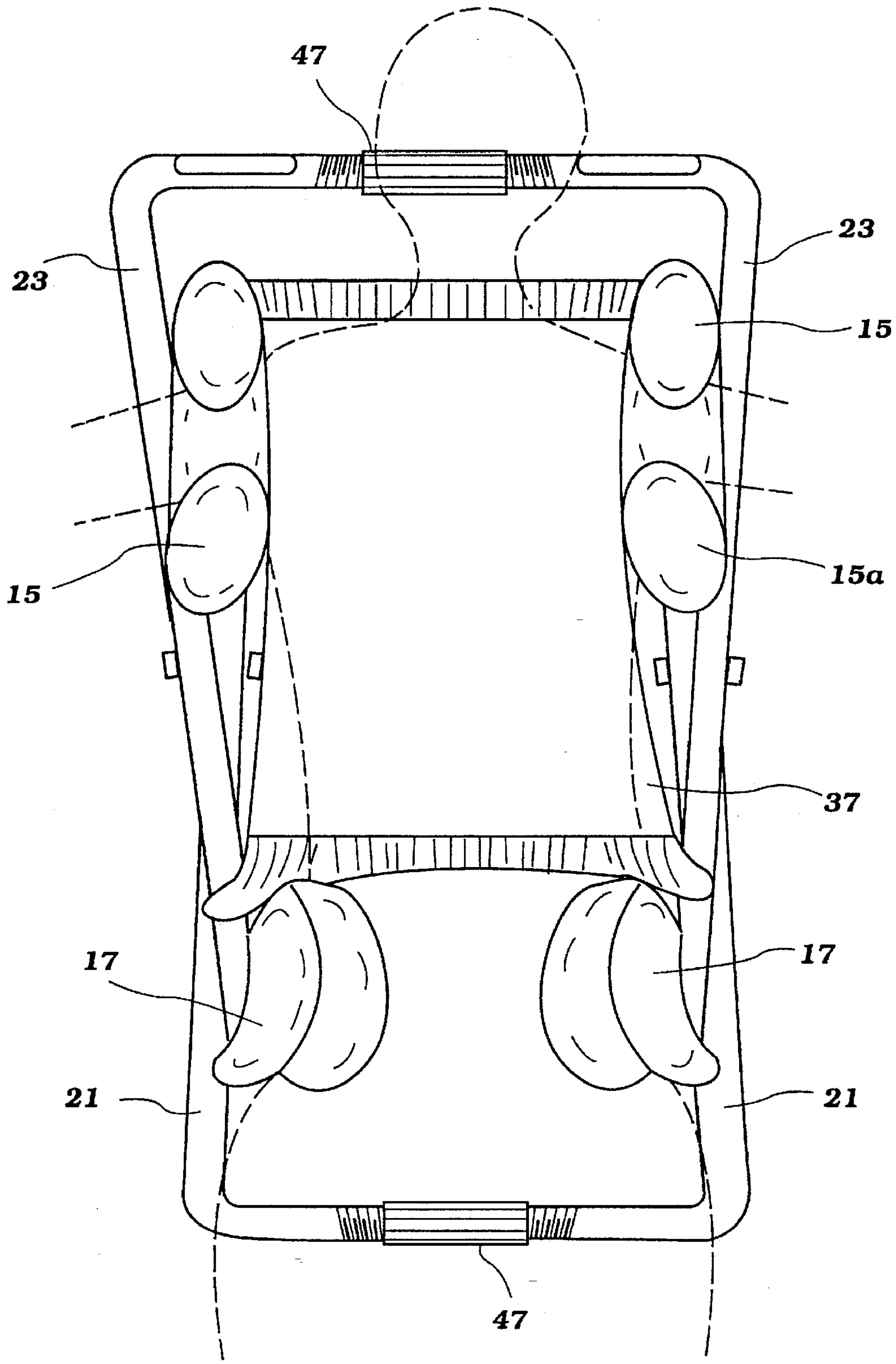
Figure 5:
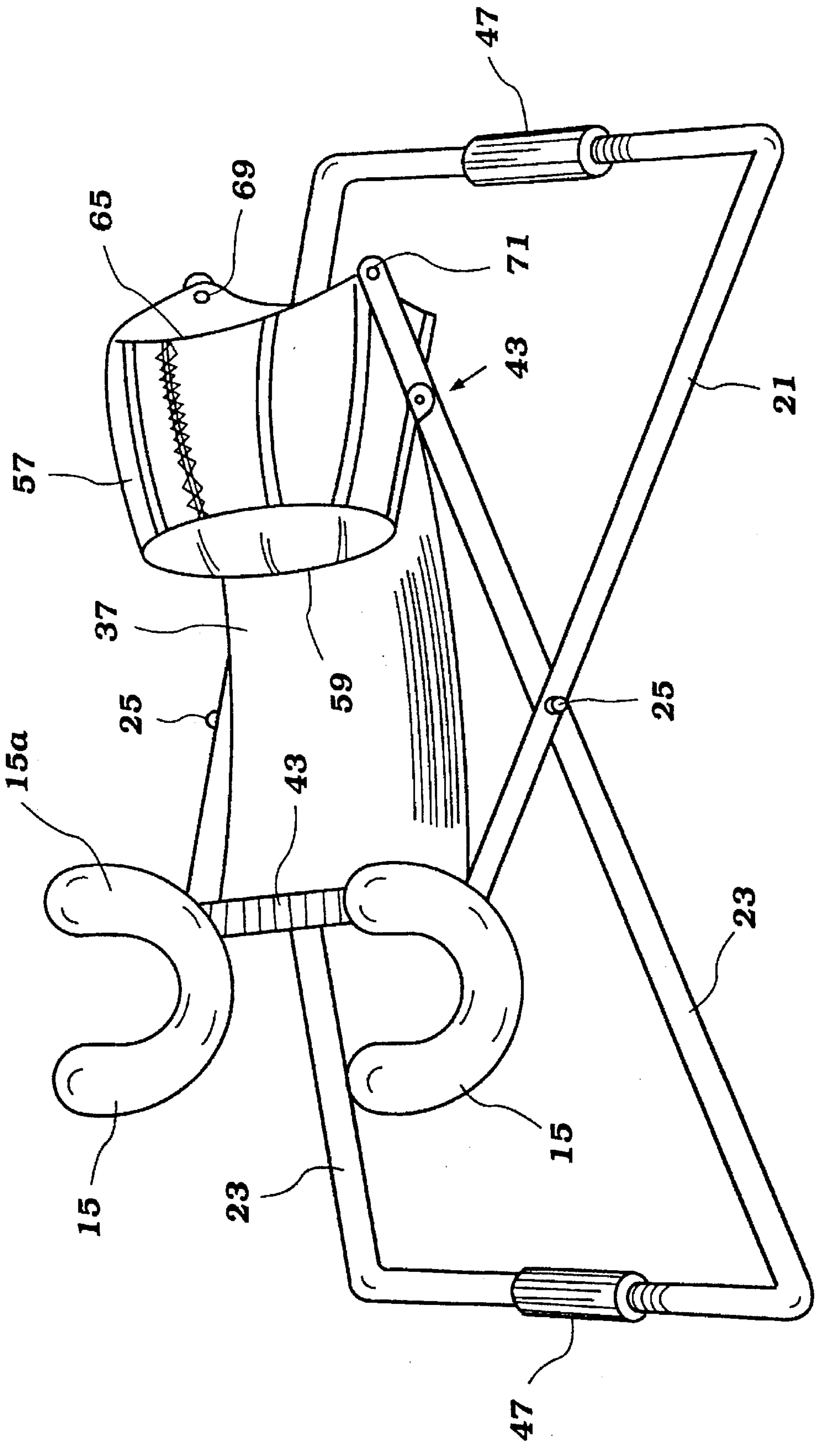
Figure 6:
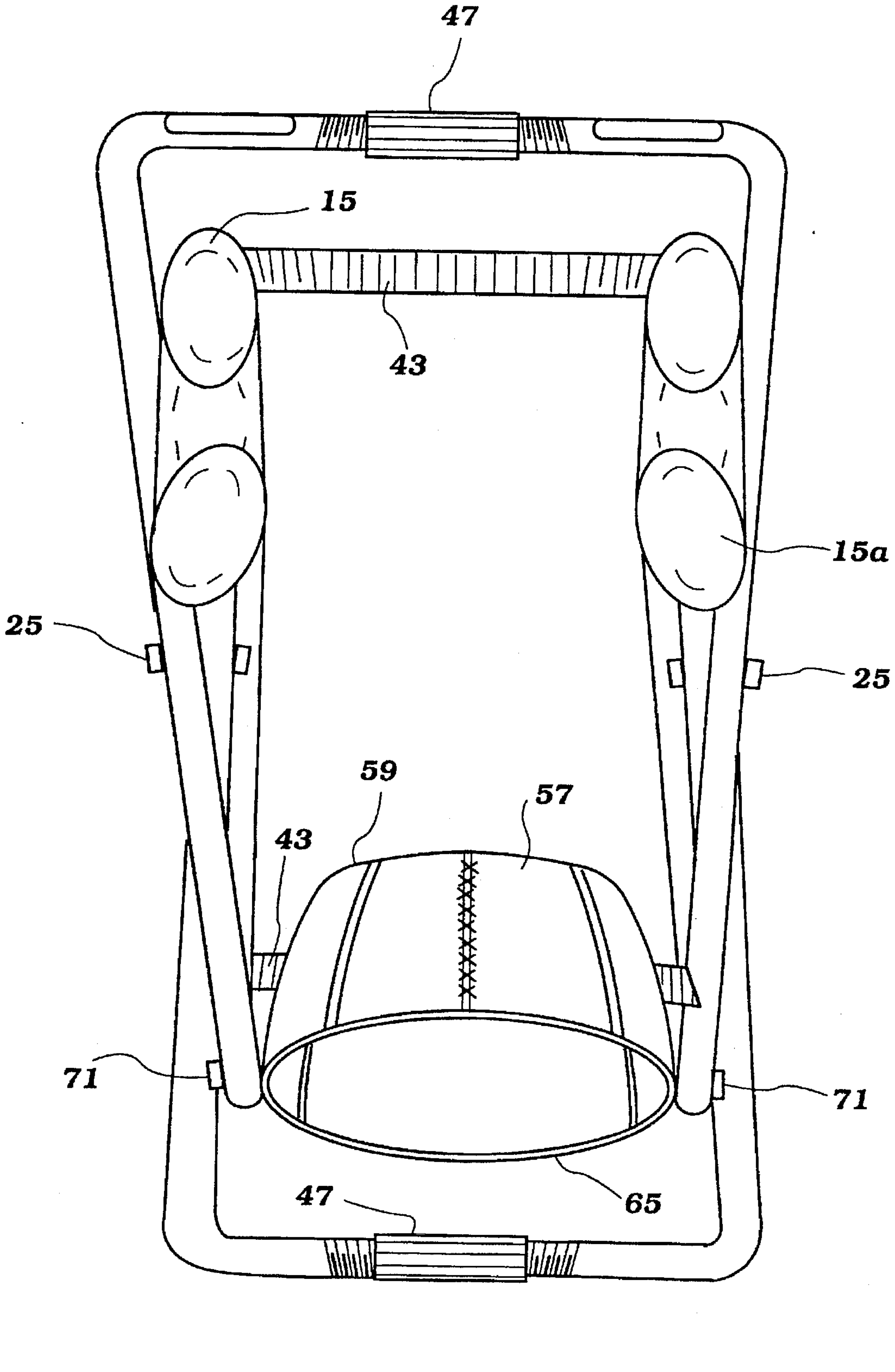
Figure 7:
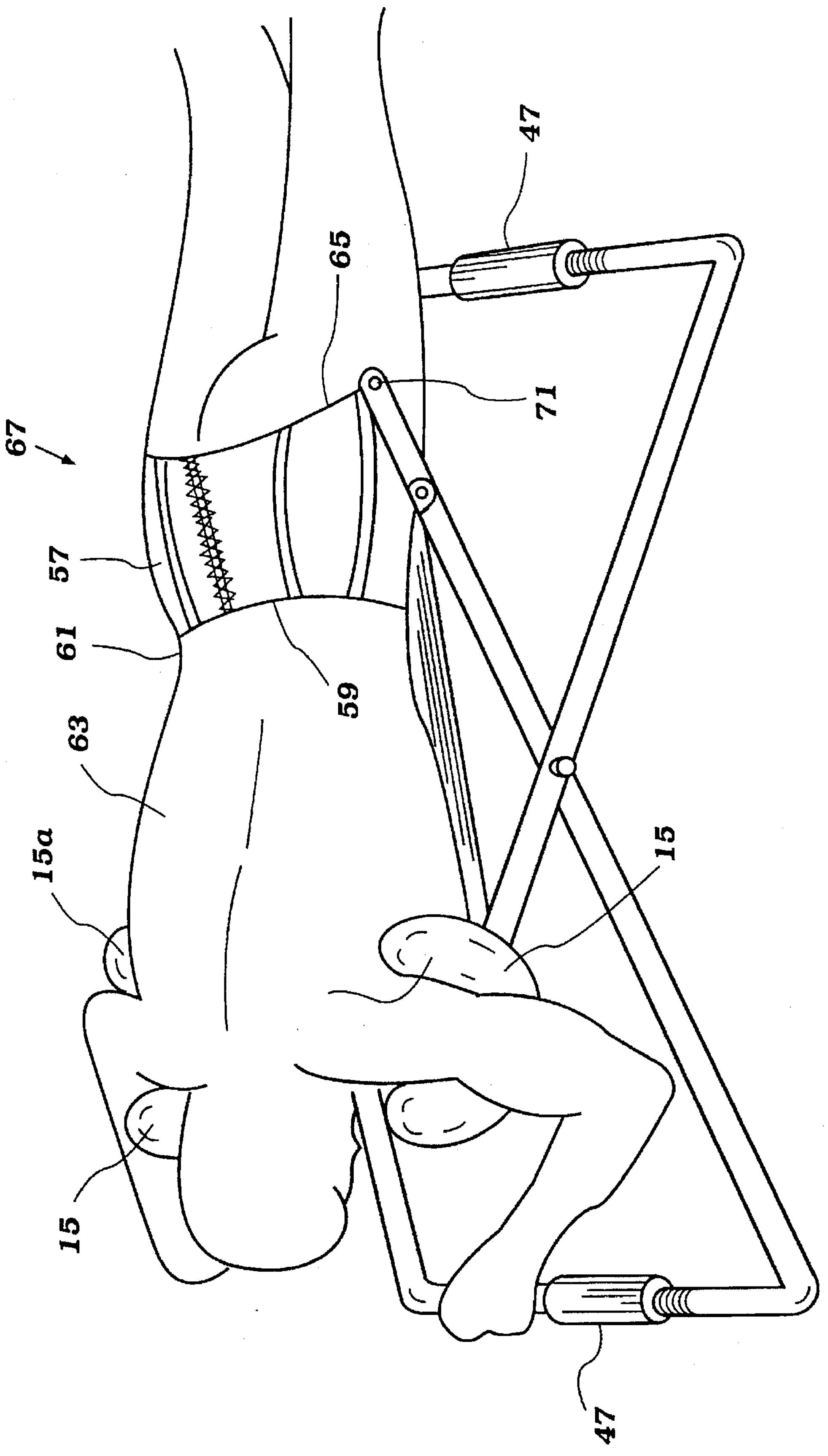
Figure 8:
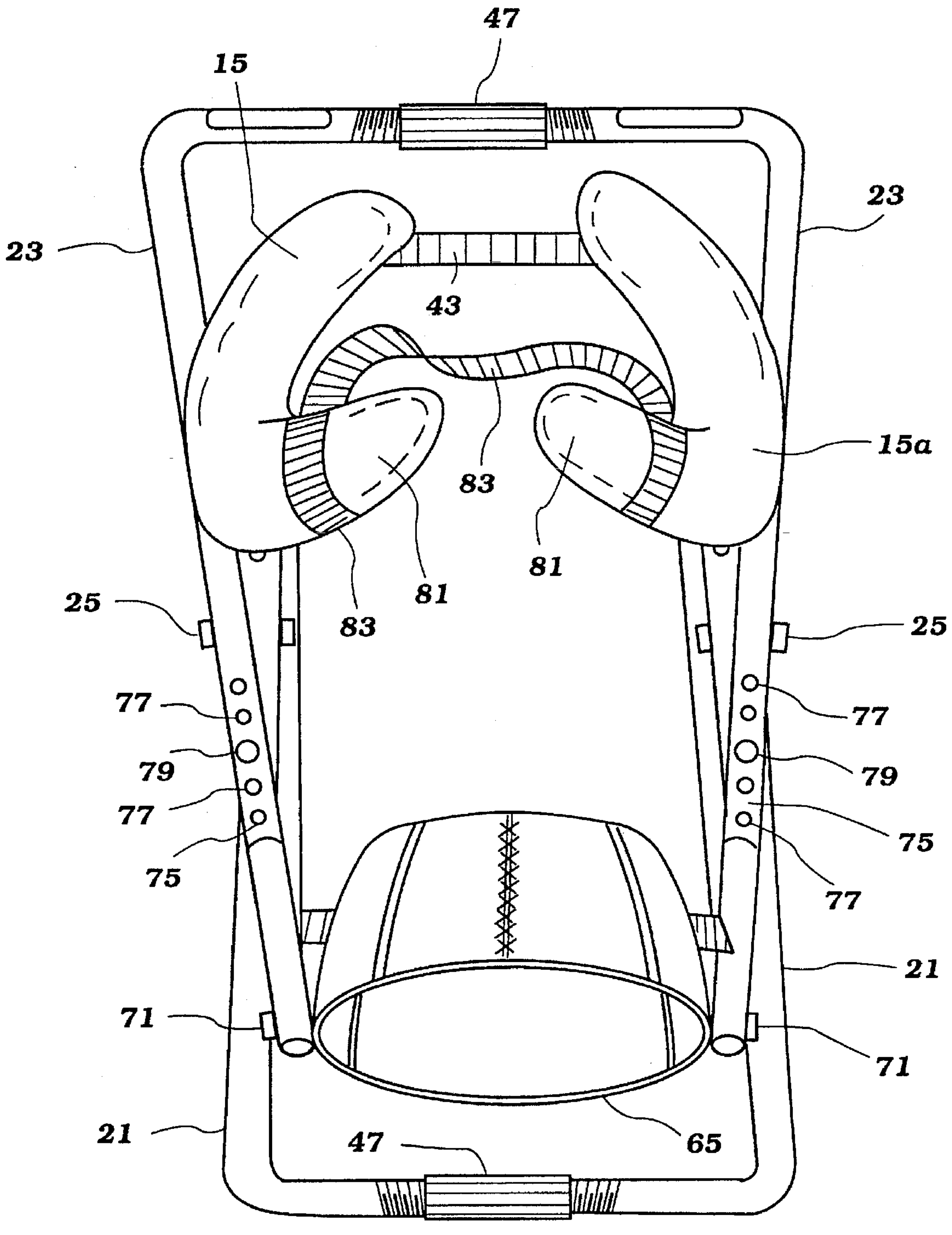
Figure 9:
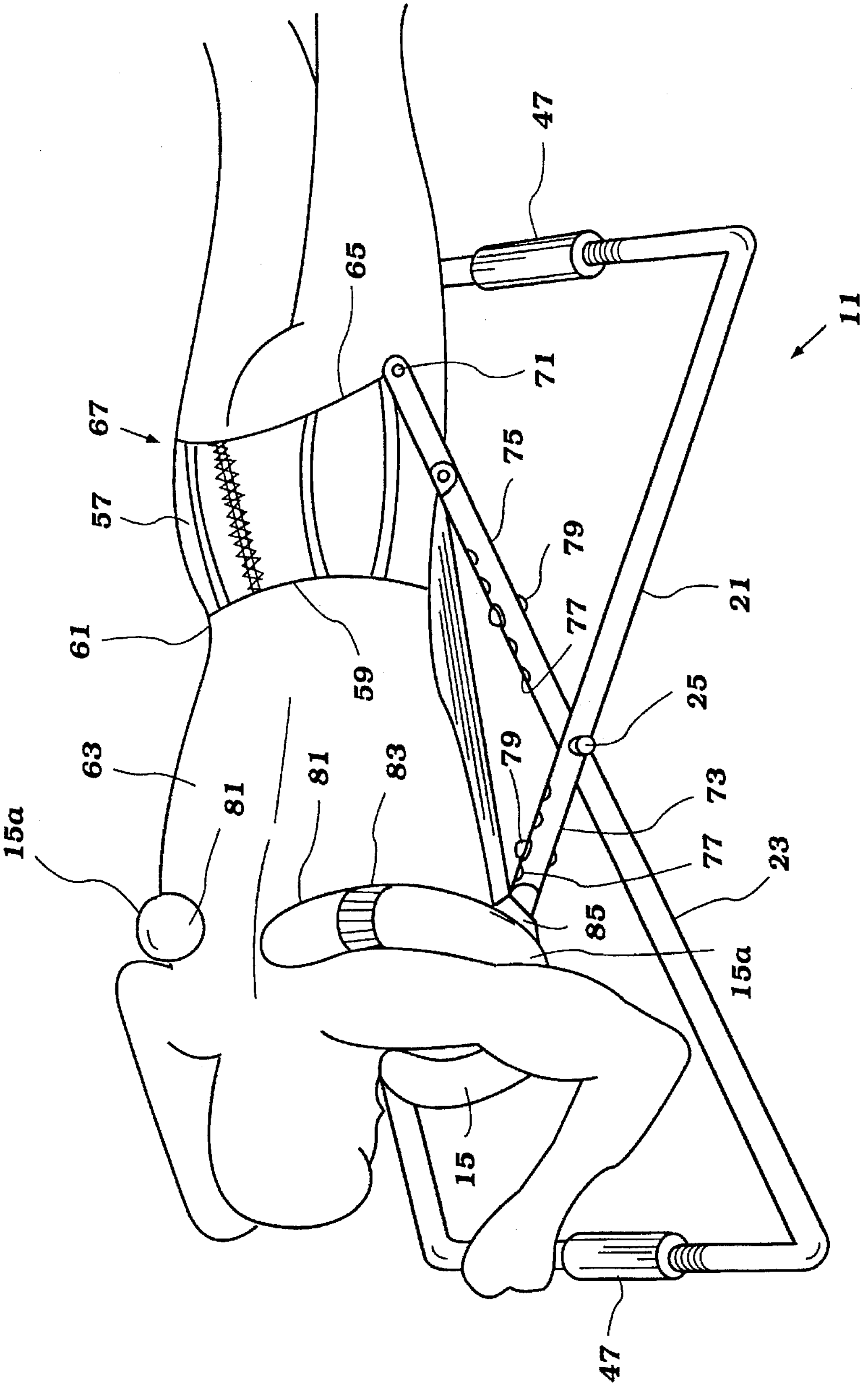
Figure 10:
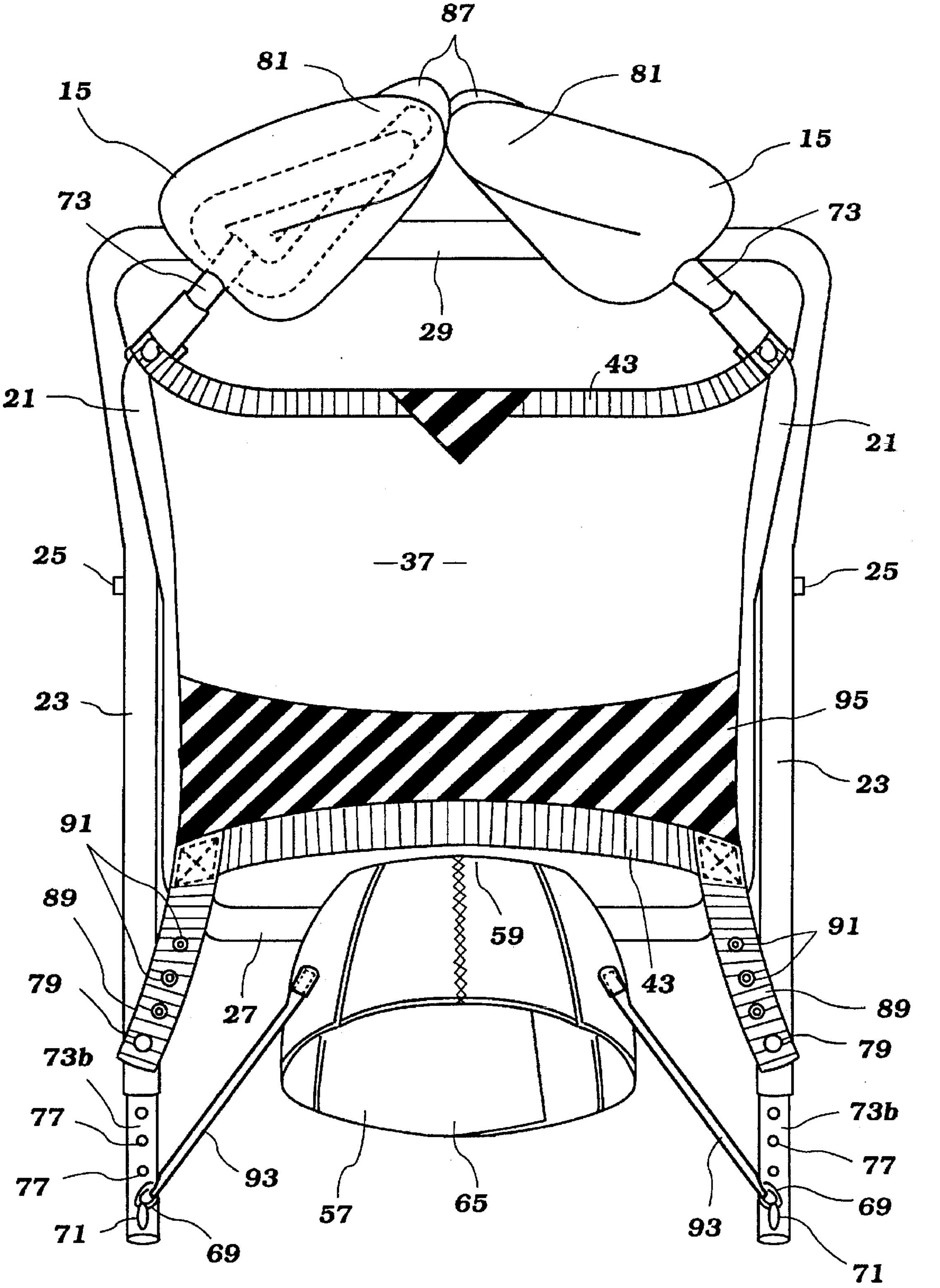
Figure 11:
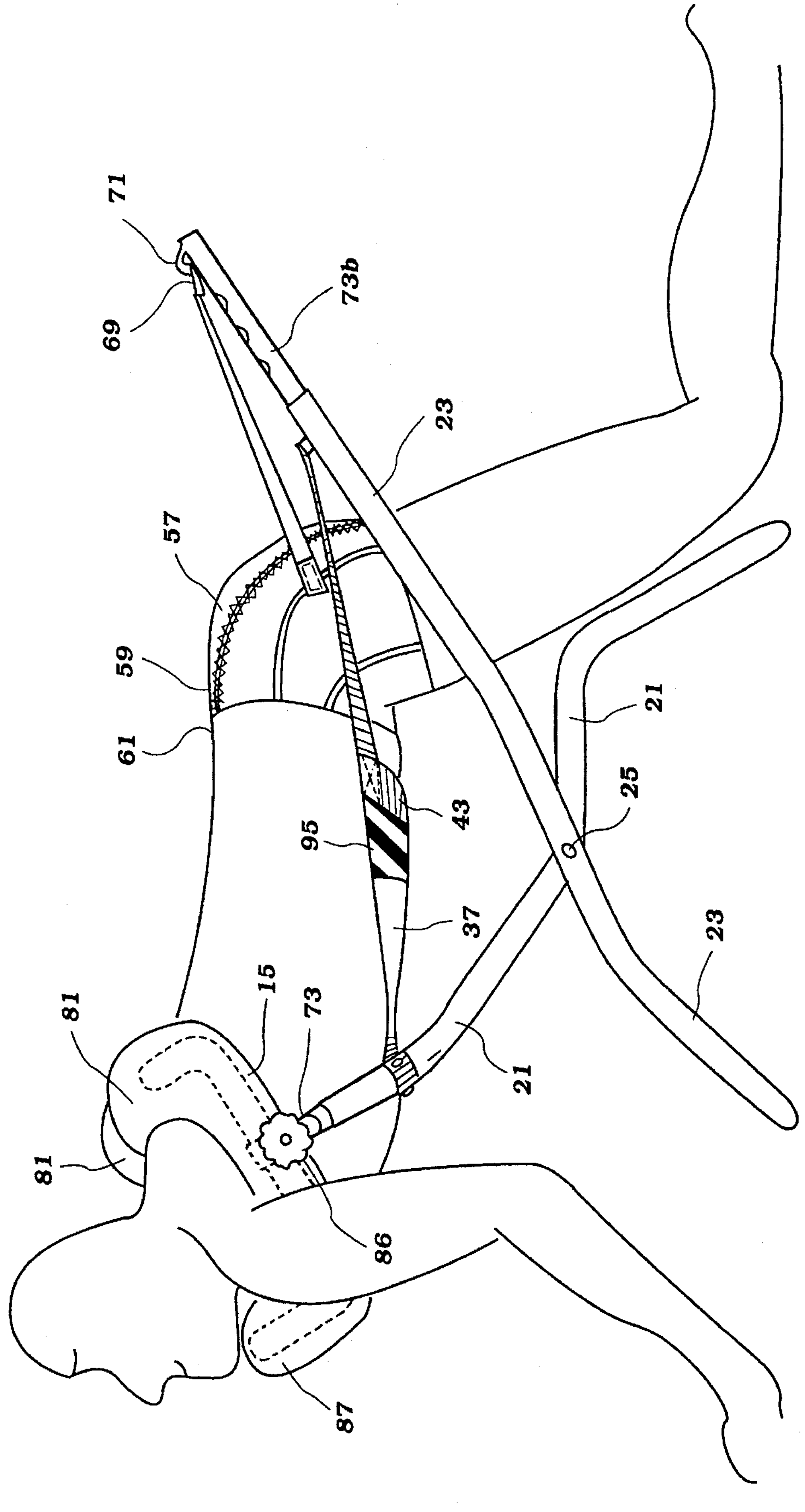

FIG. 4*a* is a plan view of the traction apparatus of FIG. 3, illustrating the traction apparatus in use;

FIG. 5 is a perspective view of a traction apparatus according to the third embodiment;

FIG. 6 is a plan view of a traction apparatus according to the third embodiment;

FIG. 7 is a perspective view showing the third embodiment in use;

FIG. 8 is a plan view of a traction apparatus according to the fourth embodiment;

FIG. 9 is a perspective view showing the fourth embodiment in use;

FIG. 10 is a plan view of a traction apparatus according to the fifth and most preferred embodiment; and FIG. 11 is a side view showing the fifth embodiment in use.

Figure 1:
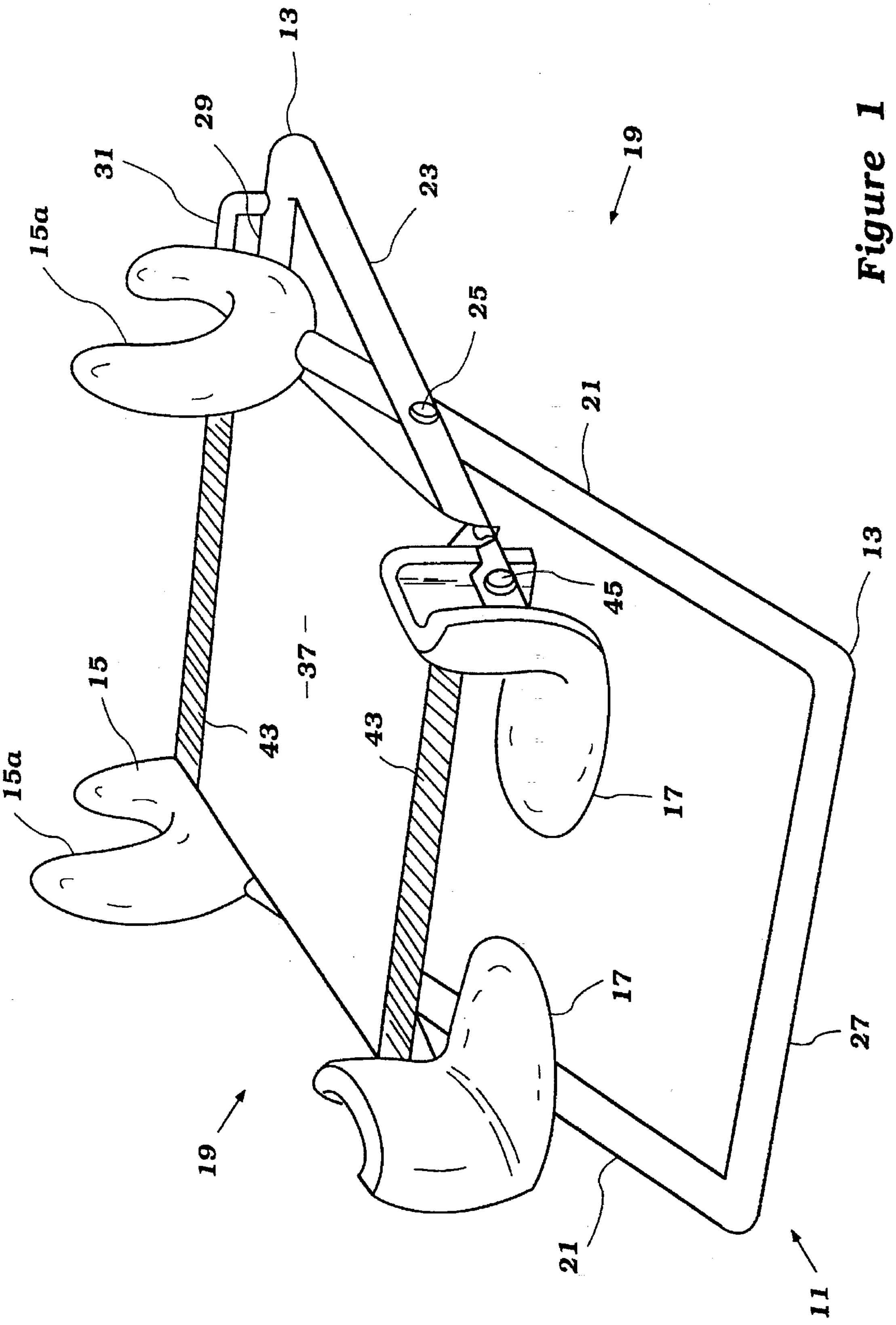
FIG. 1 is a perspective view of a traction apparatus according to the first embodiment.
Figure 2:
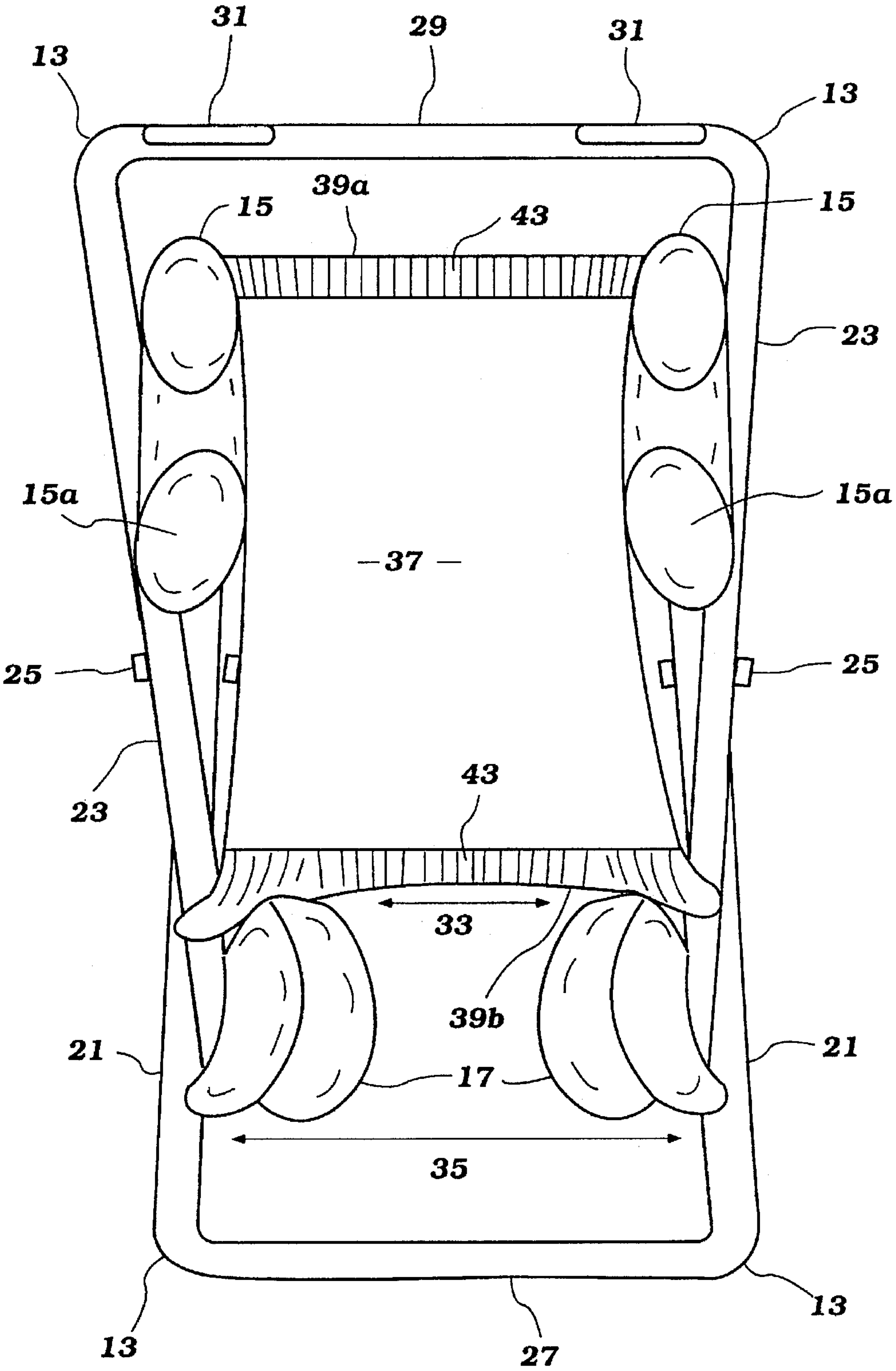
FIG. 2 is a plan view of the traction apparatus shown in FIG. 1.

The first embodiment of the traction apparatus, shown in FIGS. 1 to 3 is a back-stretch apparatus 11 which comprises a frame assembly 13 having a first tensile force application means comprising a first support in the form of two U-shaped or horseshoe shaped members 15, and a second tensile force application means comprising a second support in the form of two leaf shaped members 17.

The frame assembly 13 is conceptually two frames 19 arranged in side by side relationship, each frame comprising a first elongate strut 21 and a second elongate strut 23 connected about a pivot pin 25. The pivot pins 25 of each frame 19 may be considered to be spatially arranged about a single axis. The first elongate strut 21 and second elongate strut 23 of each frame 19 form a scissor-type arrangement. Thus there are a pair of first elongate struts 21 and a pair of second elongate struts 23, each first elongate strut 21 and second elongate strut being movably joined about a pivot pin 25 which defines an axis.

Each first elongate strut 21 is joined by a footing 27, and each second elongate strut 23 is joined by a footing 29, located at the lower end of the frame assembly 13. The footing 29 has a pair of handles 31, which are optional and provided for ease of transportation or moving of the back-stretch apparatus 11.

Each first elongate strut 21 is joined at its upper end thereof to one horseshoe shaped member 15 of the first support. Each second elongate strut 23 is joined at its upper end to one of the leaf shaped members 17 of the second support.

Each of the horseshoe shaped members 15 is formed of a U-shaped frame (which may be seen in dotted outline with reference to the fifth embodiment shown in FIG. 10), covered by padding, and optionally covered with any suitable upholstery fabric such as leather, vinyl or cloth.

The leaf shaped members 17 are constructed of a moulded core (not shown) which has been suitably upholstered, and is substantially in the shape of that region of the human body where the abdomen broadens out to the hips. Thus, (see FIG. 2) the distance separating the leaf shaped members 17 at a position 33 closest to the horseshoe shaped members 15 is narrower than the distance separating the leaf shaped members at a second position 35 more distant from the horseshoe shaped members 15. The difference in distances 33 and 35 correspond to the difference between the relative sizes of the abdomen immediately above the hips, and the abdomen in proximity to the hips respectively, in the human body. The leaf shaped members 17 so constructed will be able to engage the hips of a person, and not slip downwards, providing that the distances 33 and 35 are correct for the size of the hips of the person concerned.

The upholstery for the leaf shaped members 17, as they are shown in these embodiments, is optional, and is provided in order to provide a measure of comfort. In some applications a simple leaf shaped member finished from moulded plastic material would be sufficient.

Extending between the first elongate struts 21 in proximity to the horseshoe shape members 15, and the second elongate struts 23 in proximity to the leaf shape members is a limiting means in the form of a mat 37. The mat 37 has its width **39*a* extending between the horseshoe shaped members 15, and its width 39*b* extending between the leaf shaped members 17. The mat extends length wise between the horseshoe shaped members 15 and the leaf shaped members 17. The mat 37 limits to a maximum, the longitudinal separation of the horseshoe shaped members 15 from the leaf shaped members 17, and could also be formed of straps or other suitable means, and may be connected to the frame assembly 13 below the pivot pins 25, in an alternative constructions. However, being formed of a mat and located above the pivot pins 25 the limiting means also serves as a support for the chest and abdomen of a person using the back-stretch apparatus 11**, as will be seen from the discussion which follows.

The limiting means is preferably formed of a resilient material, and may be comprise a coil spring arrangement if the limiting means is located in a position below the pivot points 25. Thus, the mat 37 is preferably of a material resiliently stretchable at least in the longitudinal direction between the horseshoe shaped members 15 and the leaf shaped members 17, and may be resiliently stretchable normal to its longitudinal direction.

The mat 37 is provided with two strap portions 43, one extending between each horseshoe shaped member 15, and the other extending between each leaf shaped member 17. The strap portions 43 are non-elastic or at least less elastic than the mat 37 is stretchable in a direction across its width (normal to its longitudinal direction). Some elasticity in the strap portions 43 is desirable in order to accommodate the body of a person using the back stretch apparatus without causing the members 15 to be drawn together too tightly, and the members 17 to be drawn together too tightly, due to the body of the person displacing the strap portions 43 downwardly. Alternatively, the mat 37 could be mounted differently to avoid this difficulty, perhaps by mounting it lower relative to the position of the members 15 and 17.

As may be seen in FIG. 1, the leaf shaped members 17 are secured to the upper portion of the second elongate strut 23 by a bolt 45, which engages a complementary threaded aperture (not shown) in the leaf shaped members 17. Each bolt mechanism 45 may be replaced by an adjusting mechanism, to enable the leaf shaped members 17 to be adjusted to compensate for the differing waist and hip widths of different individuals. However, in the first embodiment, the distance separating the horseshoe shaped members 15 is fixed, thus the back-stretch apparatus 11 made according to the first embodiment would need to be constructed to suit specific broadness of shoulders of potential users.

The frame assembly 13 is formed of tubular steel, selected of suitable dimensions to provide a flexibility and resilience in the frame assembly, and enable the horseshoe shaped members 15 to be drawn towards each other, and the leaf shaped members 17 to be drawn towards each other, when the back-stretch apparatus 11 is in use. This flexing would be caused by the weight of a person using the back-stretch apparatus 11, and will assist in the back-stretch apparatus grasping the person using it.

In use, the back-stretch apparatus 11 is placed with its footings 27 and 29 on a suitable horizontal floor, and a user engages his waist in the leaf shaped members, and engages the horseshoe shaped members 15 around his shoulders, with the rearward portions 15*a* thereof being engaged in his armpits. The weight of the person, with his or her center of gravity being spatially located between the horseshoe shaped members 15 and the leaf shaped members 17, causes the horseshoe shaped members 15 to be drawn away from the leaf shaped members 17, thus exerting a tensile force between these members, and applying a stretching effect to the back of the person so reposed in the back-stretch apparatus 11. This can be seen in FIG. 4*a*, and although FIG. 4*a* is a different embodiment, the operating principle is the same.

The second embodiment illustrated in FIGS. 3, 4 and 4*a* differs from the first embodiment insofar as first and second adjustment means comprising adjustment mechanisms in the form of two adjusters 47 is provided. The footings 27 and 29 are divided into two separate members joined to or formed integral with the respective elongate struts 21 and 23. The adjuster 47 is a sleeve having internal threads cut therein, having a left hand thread at one end thereof, and a right hand thread at the other end thereof. Referring to FIG. 3, the left hand portion 27*a* of the footing 27 is formed with a right hand thread 49 at its end, and is threadingly engaged in a complementary thread included in the adjuster 47. The right hand portion 27*b* of the footing 27 is formed with a left hand thread 51 which is similarly received in the adjuster 47. The left hand portion 29*a* of the footing 29 is formed with a left hand thread 53, and the right hand portion 29*b* of the footing 29 is formed with the right hand thread 55.

By rotation of the adjusters, the spacing between the horseshoe shaped members 15 forming the first support may be altered, and the spacings between the leaf shaped members 17 forming the second support may be altered. Specifically, rotation of the adjuster 47*a* will alter the distance between the horseshoe shaped members 15, and rotation of the adjuster 47*b* will alter the spacing between the leaf shaped members 17. While this form of adjuster is shown, any other type of adjustment mechanism which can achieve the same effect, will be equally suitable.

In this embodiment, it may be advantageous to have some adjustment built into the strap portions 43, to accommodate different width settings allowed for by the adjusters 47. In use, the same effect as the first embodiment is achieved, but the back-stretch apparatus 11 has greater flexibility to accommodate persons of different frame or stature, due to the incorporation of the adjusters 47.

Referring to FIG. 5, 6 and 7, the third embodiment is shown. The third embodiment differs from the previous embodiments insofar as that the leaf shaped members 17 have been replaced by a detachable pelvic belt 57. A sacral pelvic traction belt such as that sold under the trade mark "DePuy" may be suitably employed for this purpose. The belt 57 is selected for correct fit for the user. Its upper circumference 59 is adapted to fit snugly around the waist 61 of a person 63, while its lower circumference 65 will snugly accommodate the hips of a person. The belt 57 is provided with a releasable fastener 69 on each side thereof which is adapted to engage a complementary fastener 71 located on the upper portion of the second elongate strut 23. Thus, when a person is accommodated in the back-stretch apparatus 11 as shown in FIG. 7, the force applied by the weight of the person 63 reposed in the back-stretch apparatus 11 will be translated into a tensile force exerted between the horseshoe shaped members 15, which are accommodated under the arms and around the shoulder of the person; and the belt 57 which is securely fitted to the person so as to not be able to slip from the waist and hips of the person. In the embodiment using the belt 57, the function of the strap portion 43 located in proximity thereto is not so important, and therefor may be deleted if desired.

It should be noted that the frames in the second and third embodiments should also be more rigid, particularly in the footings 27 and 29, than the frame in the first embodiment, as due to the adjusters 47 being provided, flexure in the frame is not required to the same extent, and indeed may be undesirable.

The the fourth embodiment, which is preferred over the embodiments heretofore described is shown in FIGS. 8 and 9. This embodiment shares features with the third embodiment except in the following respects. The first elongate struts 21 each include a first adjustment means in the form of an adjustable strut 73 arranged telescopically with the upper end of the first elongate strut, and similarly the second elongate struts 23 each include a second adjustment means in the form of a further adjustable strut 75 arranged telescopically with the upper end of the second elongate strut. The telescopic portions each include a plurality of apertures 77 extending therethrough at spaced apart intervals so that an aperture (not shown) in the upper portions of the elongate struts may be aligned therewith for insertion of a bolt 79 (or other suitable pin or the like) for adjusting the lengths of the setting the lengths of the elongate struts. In this manner, persons of different height and torso length may be accommodated by effectively adjusting the length of the elongate struts 21 and 23 to displace the first and second supports with respect to the pivot pins 25.

The horseshoe shaped members 15 have been modified by the addition of restraining portions 81 which are shaped to allow them to snugly push against the flat part of the scapulae of the person using the traction apparatus. To urge the restraining portions 81 downwardly against the scapulae, a resilient belt 83 is provided between each restraining portion 81. In use this belt will extend under tension from behind the person, under their arms and across the chest, the tension ensuring that the restraining portions 81 are held down when the person is using the traction apparatus. This tension helps hold the shoulders of the person back, giving a better posture, than the first tensile force application means or first supports hereinbefore described.

The weight of the person incident at their shoulders is taken through the belt 83 and the strap portions 43.

Finally, the horseshoe shaped members 15 have each been mounted pivotally on a ball and socket joint 85 joined to the upper portion of the first elongate strut 21. This enables the restraining portions 81 to be drawn apart to enable a person to "fit into" the traction apparatus. It should be appreciated that the ball and socket joint 85 may be replaced by a joint which will allow movement of the horseshoe shaped members in one plane.

Finally the fifth and most preferred embodiment is shown in FIGS. 10 and 11. This differs from the previous embodiments in many respects which differences will now be described.

The elongate struts 21 and 23 comprising the frame of the traction apparatus are curved in shape. The first elongate strut 21 has its lowermost portion extending steeply toward the ground on which the traction apparatus is placed. This provides the footing of the first elongate strut 21 with purchase on the ground. The second elongate struts 23 have their lowermost portions less steeply inclined, which results in the footing of the second elongate struts 23 sliding, while the footing of the first elongate strut 21 remains stationary, when a person commences use of the traction apparatus, as the traction apparatus takes his or her weight.

The first adjustable struts 73 are set at an angle with respect to the first elongate struts 21, to align pointing inwardly. The first adjustable struts 73 are mounted rotatably in the upper portions of the first elongate struts 21, and may if required, be made telescopically adjustable with respect to the upper ends of their respective first elongate struts 21 to provide adjustment of the positioning of the horse shoe shaped members 15 to suit differing shoulder widths of different people. Telescopic adjustment may be achieved by achieved utilising a method similar to that used for the embodiments heretofore described.

The horse shoe shaped members 15 are rotatably mounted to the first adjustable struts 73, dispensing with the ball and socket joint 85, utilised in the fourth embodiment, however there is included a hand operated fastener 86 on each horse shoe shaped member 15, to tighten the connection between the respective horse shoe shaped member 15 and first adjustable strut 73.

The restraining portions 81 of the horse shoe shaped members 15 are offset angularly from the other leg 87 thereof. This results in the belt 83 utilised in the fourth embodiment, not being required, as the downward force applied on the leg 87 by the weight of the person causes the horse shoe shaped members 15 to rotate about the strut 73, causing the restraining portions 81 to bear down on the scapulae of the person, to bring the shoulders back, and provide a good posture in the person being held in the traction apparatus.

The second adjustable struts **73*b* are telescopically arranged with the upper ends of the second elongate struts 23, and provide adjustment for various torso lengths in different people. The mat 37 has a pair of substantially inextensible straps 89 which extend from the rear thereof, for connecting to the upper portions of the second elongate struts. The straps 89 are each attached to the second elongate struts by bolts 79, which also extend through selected apertures 77 in the adjustable struts 73*b*. The straps 89 have a plurality of spaced eyelets 91, through one in each strap 89 the bolt 79 extends. By attaching the straps 89 through different eyelets 91, the distance between the horse shoe shaped members 15 and the detachable pelvic belt 57 can also be adjusted, varying the angular relationship of the first and second elongate struts and altering the tensile force between the horse shoe shaped members 15 and the detachable pelvic belt 57. This adjustment which varies the angular relationship of the first and second elongate struts differs from the adjustment made by merely telescopically adjusting the adjustable struts 73*b* with respect to the second elongate struts 23** which does not vary angular relationship of the first and second elongate struts.

The removable pelvic belt 57 is attached by a pair of substantially inextensible straps 93, to the top of the adjustable struts **73*b* via the releasable fastener 69 mounted on each strap 93 removably fitted to the fastener 71 located on the upper portion of the second elongate strut 23**.

The mat 37 differs from the mats described in the previous embodiments, insofar as the strap portions 43 are formed of non stretchable nylon webbing, stitched to the main body of the mat 37, which is formed of a substantially unstretchable inelastic fabric. The rearward part of the mat 37 comprises a section 95 of 3 mm thick vulcanised rubber sheeting, which provides sufficient stretching in both dimensions to give suitable elasticity to the mat 37. Furthermore, there is a vee shaped section 97 in the centre of the forward edge of the mat 37 to accommodate the bust without undue discomfort.

Having described the invention, it should be clear how various modifications may be made, for example the leaf shaped members 17 or sacral pelvic belt 57 may be replaced by a pair of jaws which may be adjustably operated by a mechanism placed in a convenient position, so as to enable the user to select an appropriate spacing between the jaws to accommodate his or her waist or hips. This would obviate the need for incorporating the adjuster **47*b***.

Additionally, the position of the pivot points 25 along the first and second elongate struts 21 and 23 may be made adjustable, by including apertures at various positions along the first elongate struts 21 and second elongate struts 23, in order to alter the distance between the first support and the second support, and alter the leverage exerted on the first and second supports, thus altering the tensile force applied between the same, dependent upon the weight of the person using the back-stretch apparatus 11.

The handles 31, in addition to being useful for carrying the back-stretch apparatus 11, may also be employed to enable the user to pull himself down towards the floor, and thus increase the force exerted between the first support and the second support, and increase the stretch applied by the back-stretch apparatus 11 to his or her spine.

The frame assembly 13 may be formed of material other than tubular steel. For example, the frame assembly 13 may be formed of any suitable material such as plastic, wood or fibreglass.

In addition the shape of the first support need not be horseshoe shaped. A U-shaped member is equally suitable, and in certain circumstances an upright post for engaging under the arms of a person may be suitable, in much the same manner as the rearward portions 15*b* of the horseshoe shaped members 15 function.

The back stretch apparatus provides a means by which a person may relieve back pain or discomfort, effectively, at home, and whenever desired. The back stretch apparatus will obviate the need, in many cases, for a person to seek professional traction treatment in a hospital or with a professional consultant, when the need for such treatment arises; and will allow those people who are perhaps athletically less able and unable to utilise gravity boots or inversion tables, to effectively obtain traction treatment in the comfort of their own home. Other advantages are brought about by the portability of the back stretch apparatus.

It should be appreciated that the scope of the invention should not be limited to the scope of the embodiment described herein.

The claims defining the invention are as follows:

I claim:

1. A traction apparatus for vertebral manipulation comprising a frame assembly including first and second frame members, wherein each frame member comprises two parallel elongated struts having at their lower ends a footing member which is adapted to be supported on a generally horizontal supporting surface, said frame members are pivotally connected at an intermediate location on the elongated struts in a scissor type relationship and have upward portions diverging upwardly from the pivotal connection, a first tensile force application means for engaging the body of a person in proximity to the upper thorax carried at an upper portion of one of said pivotally connected frame members, and having a second tensile force application means for engaging the body of the person in proximity to the lower lumbar region carried at an upper portion of the other of said pivotally connected frame members; said frame assembly being supported on the surface so that when the person's body is restrained by the tensile force application means, the pivotally connected frame members pivot about their pivotal connection for effecting axial movement therebetween for providing a tensile force on the body of the person generated by the weight of the person.

2. A traction apparatus as claimed in claim 1 including means for limiting the extent of movement of said first and second tensile force application means relative to each other.

3. A traction apparatus as claimed in claim 2 wherein said limiting means comprises a mat extending between upper portions of said elongate struts, said mat being resiliently deformable at least in the direction of the extent between upper portions of said first and second elongate struts.

4. A traction apparatus as claimed in claim 3 wherein said mat is also resiliently deformable a direction extending between parallel elongate struts.

5. A traction apparatus as claimed in claim 1 wherein said first tensile force application means comprises a first support means to engage the body of the person about their shoulders and armpits.

6. A traction apparatus as claimed in claim 5 wherein said first support means comprises a pair of substantially U-shaped members, one mounted on each said first elongated strut.

7. A traction apparatus as claimed in claim 5 wherein said first support means includes restraining portions adapted to abut the flat of the scapulae of the person.

8. A traction apparatus as claimed in any one of claims wherein said first support means also includes a resiliently stretchable strap extending between said restraining portions.

9. A traction apparatus as claimed in claim 5 wherein said traction apparatus includes a first adjustment means to selectively vary the positioning of said first support means.

10. A traction apparatus as claimed in claim 9 wherein said first adjustment means comprises an adjustable strut extending from said first elongate struts.

11. A traction apparatus as claimed in claim 1 wherein said second tensile force application means comprises a second support means to engage the body of the person about their hips.

12. A traction apparatus as claimed in claim 11 wherein said second support means comprises a device adapted to be fastened so as to prevent movement to a position below the hips of a wearer and adapted to be removably fastened to said second frame.

13. A traction apparatus as claimed in claim 11 wherein said second support means comprises an adjustable clamp, adapted to engage a person about their hips.

14. A traction apparatus as claimed in claim 13 wherein said clamp is formed in a shape adapted to be complementary to the hip region of a person.

15. A traction apparatus as claimed in claim 11 wherein said traction apparatus includes a second adjustment means to selectively vary the positioning of said second support means.

16. A traction apparatus as claimed in claim 15 wherein said second adjustment means comprises a further adjustable strut extending from said second elongate struts.

* * * * *